(12) United States Patent
Chind

(10) Patent No.: US 9,055,982 B2
(45) Date of Patent: Jun. 16, 2015

(54) SPINAL IMPLANT SYSTEM AND METHODS OF USE

(71) Applicant: Warsaw Orthopedic, Inc., Warsaw, IN (US)

(72) Inventor: Daniel Chind, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 196 days.

(21) Appl. No.: 13/626,010

(22) Filed: Sep. 25, 2012

(65) Prior Publication Data

US 2014/0088648 A1    Mar. 27, 2014

(51) Int. Cl.
*A61B 17/70* (2006.01)
*A61B 17/80* (2006.01)
*A61B 17/00* (2006.01)

(52) U.S. Cl.
CPC ......... *A61B 17/7071* (2013.01); *A61B 17/7067* (2013.01); *A61B 17/7052* (2013.01); *A61B 17/8042* (2013.01); *A61B 2017/00004* (2013.01)

(58) Field of Classification Search
CPC ............. A61B 17/809; A61B 17/8061; A61B 17/7052; A61B 17/7068; A61B 17/7071; A61B 17/7067
USPC .......................... 606/246, 251–253, 280–281
See application file for complete search history.

(56) References Cited

U.S. PATENT DOCUMENTS

| | | | | |
|---|---|---|---|---|
| 5,439,463 A * | 8/1995 | Lin | ................................. | 606/252 |
| 5,752,955 A * | 5/1998 | Errico | .............................. | 606/252 |
| 5,980,572 A * | 11/1999 | Kim et al. | ................... | 623/17.16 |
| 6,139,548 A * | 10/2000 | Errico | ............................. | 606/252 |
| 6,238,396 B1 * | 5/2001 | Lombardo | ................... | 606/86 A |
| 6,264,658 B1 * | 7/2001 | Lee et al. | ........................ | 606/254 |
| 6,402,751 B1 * | 6/2002 | Hoeck et al. | ................... | 606/252 |
| 6,432,108 B1 * | 8/2002 | Burgess et al. | ............... | 606/252 |
| 6,572,617 B1 * | 6/2003 | Senegas | ........................ | 606/263 |
| 6,592,585 B2 * | 7/2003 | Lee et al. | ........................ | 606/252 |
| 6,602,253 B2 * | 8/2003 | Richelsoph et al. | ........... | 606/252 |
| 6,660,007 B2 * | 12/2003 | Khanna | .......................... | 606/284 |
| 6,709,435 B2 * | 3/2004 | Lin | ................................. | 606/250 |
| 6,752,807 B2 * | 6/2004 | Lin et al. | ........................ | 606/250 |
| 6,761,721 B2 * | 7/2004 | Burgess et al. | ............... | 606/252 |
| 7,717,939 B2 * | 5/2010 | Ludwig et al. | ................ | 606/250 |
| 7,717,940 B2 * | 5/2010 | Woods et al. | .................. | 606/253 |
| 7,871,411 B2 * | 1/2011 | Grevious | ......................... | 606/60 |
| 7,892,258 B2 * | 2/2011 | Iott et al. | ........................ | 606/250 |
| 8,002,810 B2 * | 8/2011 | Osman | ........................... | 606/282 |
| 8,034,083 B2 * | 10/2011 | Abdelgany et al. | ............ | 606/257 |
| 8,043,338 B2 * | 10/2011 | Dant | ............................... | 606/252 |
| 8,172,875 B2 * | 5/2012 | Taylor | ........................... | 606/246 |
| 8,221,466 B2 * | 7/2012 | Asaad et al. | ................... | 606/252 |
| 8,231,623 B1 * | 7/2012 | Jordan | ............................ | 606/54 |
| 8,241,334 B2 * | 8/2012 | Butler et al. | ................... | 606/278 |

(Continued)

*Primary Examiner* — Eduardo C Robert
*Assistant Examiner* — Stuart S Bray

(57) ABSTRACT

A spinal implant includes a first member and a second member. The first member extends between a first end and a second end. The first end is configured for fixation with vertebral tissue adjacent a lamina. The second member extends between a first end and a second end. The first end is configured for fixation with vertebral tissue adjacent the lamina. The second end is connected to the second end of the first member. The first end of the second member is disposed in a spaced apart relation to the first end of the first member. The second ends are relatively movable in a configuration such that the members are expandable and/or contractible. Systems and methods of use are disclosed.

16 Claims, 9 Drawing Sheets

(56) References Cited

U.S. PATENT DOCUMENTS

| | | | |
|---|---|---|---|
| 8,262,701 B2* | 9/2012 | Rathbun et al. | 606/250 |
| 8,366,750 B2* | 2/2013 | Iott et al. | 606/279 |
| 8,425,515 B2* | 4/2013 | Gamache et al. | 606/70 |
| 8,425,520 B2* | 4/2013 | Zalenski et al. | 606/86 B |
| 8,449,580 B2* | 5/2013 | Voellmicke et al. | 606/279 |
| 8,470,003 B2* | 6/2013 | Voellmicke et al. | 606/279 |
| 8,608,780 B2* | 12/2013 | Forton et al. | 606/252 |
| 8,608,781 B2* | 12/2013 | Asaad et al. | 606/253 |
| 8,926,664 B1* | 1/2015 | Millhouse et al. | 606/246 |
| 2002/0032442 A1* | 3/2002 | Altarac et al. | 606/61 |
| 2002/0143330 A1* | 10/2002 | Shluzas | 606/61 |
| 2002/0183749 A1* | 12/2002 | Burgess et al. | 606/61 |
| 2003/0018334 A1* | 1/2003 | Richelsoph et al. | 606/61 |
| 2003/0028192 A1* | 2/2003 | Schar et al. | 606/61 |
| 2003/0050640 A1* | 3/2003 | Lee et al. | 606/61 |
| 2003/0050700 A1* | 3/2003 | Kihara | 623/17.11 |
| 2003/0083659 A1* | 5/2003 | Lin et al. | 606/61 |
| 2003/0114853 A1* | 6/2003 | Burgess et al. | 606/61 |
| 2003/0125738 A1* | 7/2003 | Khanna | 606/61 |
| 2003/0153914 A1* | 8/2003 | Oribe et al. | 606/61 |
| 2003/0191470 A1* | 10/2003 | Ritland | 606/61 |
| 2004/0030388 A1* | 2/2004 | Null et al. | 623/17.11 |
| 2004/0049188 A1* | 3/2004 | Slivka et al. | 606/61 |
| 2004/0210222 A1* | 10/2004 | Angelucci et al. | 606/69 |
| 2005/0090821 A1* | 4/2005 | Berrevoets et al. | 606/61 |
| 2005/0107877 A1* | 5/2005 | Blain | 623/16.11 |
| 2005/0119657 A1* | 6/2005 | Goldsmith | 606/61 |
| 2005/0131412 A1* | 6/2005 | Olevsky et al. | 606/69 |
| 2005/0228326 A1* | 10/2005 | Kalfas et al. | 602/19 |
| 2005/0228377 A1* | 10/2005 | Chao et al. | 606/61 |
| 2005/0251138 A1* | 11/2005 | Boris et al. | 606/61 |
| 2005/0273100 A1* | 12/2005 | Taylor | 606/61 |
| 2007/0225717 A1* | 9/2007 | Hawkes | 606/69 |
| 2008/0109039 A1* | 5/2008 | Michielli et al. | 606/251 |
| 2008/0215096 A1* | 9/2008 | Nash et al. | 606/249 |
| 2009/0093820 A1* | 4/2009 | Trieu et al. | 606/103 |
| 2009/0228046 A1* | 9/2009 | Garamszegi | 606/278 |
| 2009/0318968 A1* | 12/2009 | Duggal et al. | 606/250 |
| 2010/0036420 A1* | 2/2010 | Kalfas et al. | 606/250 |
| 2010/0057127 A1* | 3/2010 | McGuire et al. | 606/246 |
| 2010/0069960 A1* | 3/2010 | Chaput | 606/249 |
| 2010/0121381 A1* | 5/2010 | Berta et al. | 606/264 |
| 2010/0185239 A1* | 7/2010 | Patel et al. | 606/246 |
| 2010/0185240 A1* | 7/2010 | Mangione et al. | 606/250 |
| 2010/0191289 A1* | 7/2010 | Ludwig et al. | 606/264 |
| 2010/0198221 A1* | 8/2010 | Hearn | 606/71 |
| 2010/0204733 A1* | 8/2010 | Rathbun et al. | 606/251 |
| 2011/0046675 A1* | 2/2011 | Barrus et al. | 606/252 |
| 2011/0046680 A1* | 2/2011 | Khanna | 606/279 |
| 2011/0125193 A1* | 5/2011 | Grevious | 606/280 |
| 2012/0035659 A1* | 2/2012 | Barrus et al. | 606/251 |
| 2012/0071931 A1* | 3/2012 | Perez-Cruet et al. | 606/279 |
| 2012/0078304 A1* | 3/2012 | Jensen et al. | 606/251 |
| 2012/0101529 A1* | 4/2012 | Ludwig et al. | 606/264 |
| 2012/0109201 A1* | 5/2012 | Kretzer et al. | 606/248 |
| 2012/0158060 A1* | 6/2012 | Abrahams et al. | 606/248 |
| 2012/0165942 A1* | 6/2012 | Khanna | 623/17.16 |
| 2012/0179204 A1* | 7/2012 | Rathbun et al. | 606/252 |
| 2012/0271359 A1* | 10/2012 | Stevenson et al. | 606/281 |
| 2012/0283780 A1* | 11/2012 | Ludwig et al. | 606/270 |
| 2012/0316647 A1* | 12/2012 | Farin | 623/17.13 |
| 2013/0060283 A1* | 3/2013 | Suh et al. | 606/246 |
| 2013/0150888 A1* | 6/2013 | James | 606/251 |
| 2013/0197641 A1* | 8/2013 | Shepard et al. | 623/17.11 |
| 2013/0253586 A1* | 9/2013 | Rathbun et al. | 606/251 |
| 2013/0345814 A1* | 12/2013 | Walkenhorst et al. | 623/17.16 |
| 2014/0012320 A1* | 1/2014 | Ludwig et al. | 606/270 |
| 2014/0088651 A1* | 3/2014 | Ludwig et al. | 606/268 |
| 2014/0257487 A1* | 9/2014 | Lawson et al. | 623/17.16 |
| 2014/0257491 A1* | 9/2014 | Parry et al. | 623/17.16 |
| 2014/0296982 A1* | 10/2014 | Cheng | 623/17.16 |
| 2014/0336770 A1* | 11/2014 | Petersheim et al. | 623/17.16 |
| 2014/0371859 A1* | 12/2014 | Petersheim et al. | 623/17.16 |

* cited by examiner

SPINAL IMPLANT SYSTEM AND METHODS OF USE

TECHNICAL FIELD

The present disclosure generally relates to spinal implant devices for the treatment of musculoskeletal disorders, and more particularly to a surgical system that includes a spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy, laminoplasty and implantable prosthetics. For example, laminoplasty treatments may employ implants, which may include plates and bone fasteners to stabilize vertebrae and facilitate healing. This disclosure describes an improvement over these prior art technologies.

SUMMARY

In one embodiment, a spinal implant is provided. The spinal implant includes a first member and a second member. The first member extends between a first end and a second end. The first end is configured for fixation with vertebral tissue adjacent a lamina. The second member extends between a first end and a second end. The first end is configured for fixation with vertebral tissue adjacent the lamina. The second end is connected to the second end of the first member. The first end of the second member is disposed in a spaced apart relation to the first end of the first member. The second ends are relatively movable in a configuration such that the members are expandable and/or contractible.

BRIEF DESCRIPTION OF THE DRAWINGS

The present disclosure will become more readily apparent from the specific description accompanied by the following drawings, in which.

DETAILED DESCRIPTION

Figure 1:
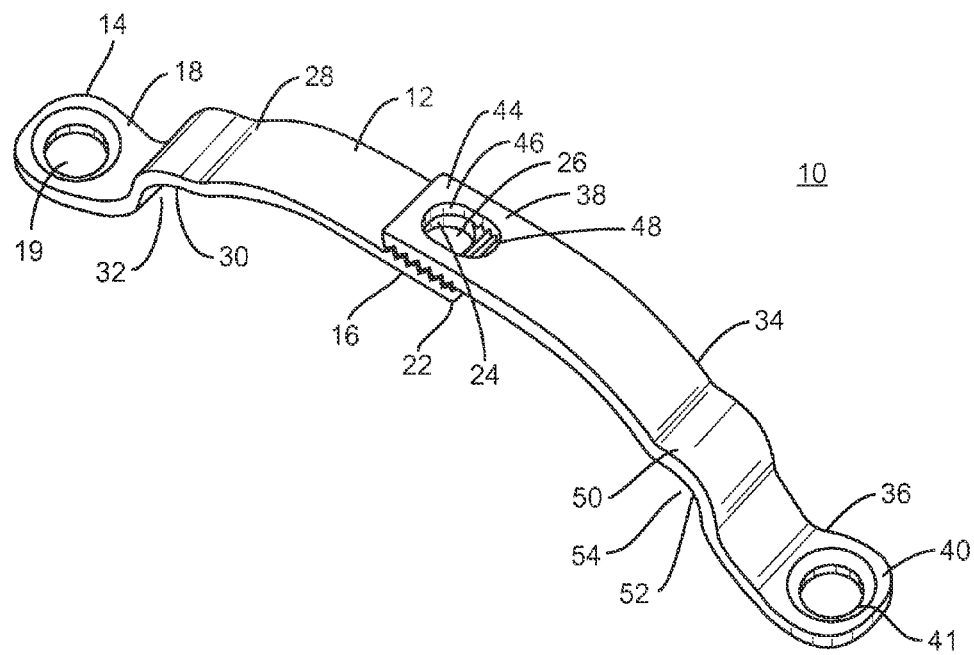
FIG. 1 is a perspective view of components of one particular embodiment of a system in accordance with the principles of the present disclosure.
Figure 2:
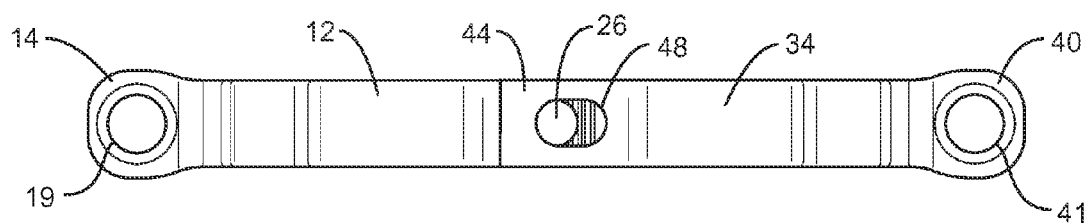
FIG. 2 is a plan view in part cross section of the components shown in FIG. 1.
Figure 3:
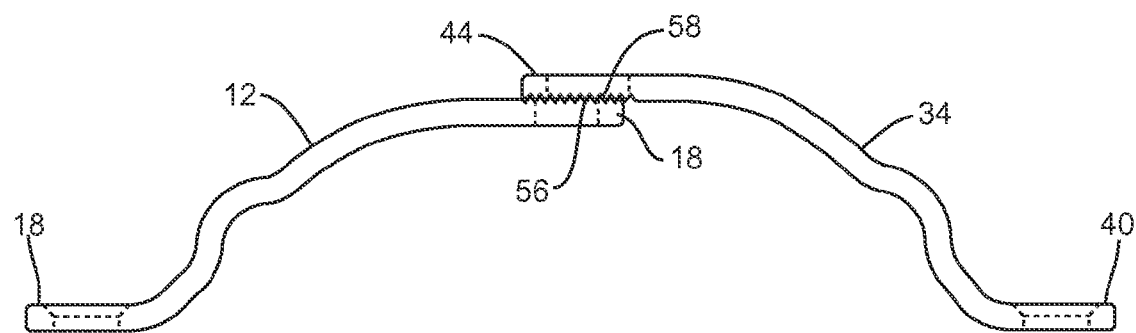
FIG. 3 is a side view of the components shown in FIG. 1, in part phantom.
Figure 4:
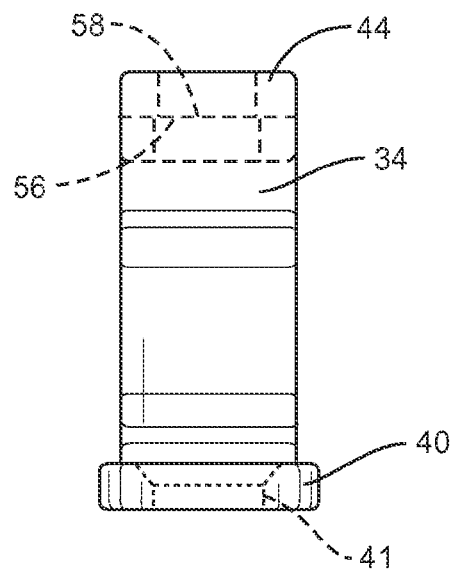
FIG. 4 is a side view of the components shown in FIG. 1, in part phantom.

The exemplary embodiments of the surgical system and related methods of use disclosed are discussed in terms of medical devices for the treatment of musculoskeletal disorders and more particularly, in terms of a surgical system that includes a spinal implant and a method for treating a spine. In one embodiment, the systems and methods of the present disclosure are employed with a laminoplasty procedure.

In one embodiment, the surgical system includes an adjustable width implant. In one embodiment, the surgical system includes an implant having plates with apertures that are configured to provide clearance under each plate for a tool to cut the lamina once the plate is attached. In one embodiment, the surgical system includes a dual laminoplasty stabilization implant that is fixed to the bone prior to cutting. In one embodiment, the surgical system is employed with a method such that bone is cut and the implant allows for adjustment and expansion. In one embodiment, the implant bridges the spinous process allowing both lamina to be cut while remaining centered over the spinous process. It is contemplated that adjustment of the implant allows for expansion to relieve compression of the spine. In one embodiment, the spinous process may require trimming for proper adjustment and compression relief. In one embodiment, the adjusted implant can be secured via a screw or ratchet configuration.

It is envisioned that the present disclosure may be employed to treat spinal disorders such as, for example, degenerative disc disease, disc herniation, osteoporosis, spondylolisthesis, stenosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including posterior, posterior midline, medial, lateral, postero-lateral approaches, and in other body regions. The surgical system and methods of the present disclosure may also be alternatively employed with procedures for treating the lumbar, cervical, thoracic and pelvic regions of a spinal column. The implant and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-7, there is illustrated components of a surgical system including a spinal implant 10 in accordance with the principles of the present disclosure.

The components of the surgical system can be fabricated from biologically acceptable materials suitable for medical applications, including metals, synthetic polymers, ceramics and bone material and/or their composites, depending on the particular application and/or preference of a medical practitioner. For example, the components of the surgical system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (for example, Nitinol, super elasto-plastic metals, such as GUM METAL® manufactured by Toyota Material Incorporated of Japan), ceramics and composites thereof such as calcium phosphate (for example, SKELITE™ manufactured by Biologix Inc.), thermoplastics such as polyaryl ether ketone (PAEK) including polyether ether ketone (PEEK), polyether ketone ketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polylactide, polyglycolide, polytyrosine carbonate, polycaprolactone and their combinations. Various components of the surgical system may be fabricated from material composites, including the above materials, to achieve various desired characteristics such as strength, rigidity, elasticity, flexibility, compliance, biomechanical performance, durability and radiolucency or imaging preference. The components of the surgical system, individually or collectively, may also be fabricated from a heterogeneous material such as a combination of two or more of the above-described materials.

The surgical system including spinal implant 10 can be employed, for example, in laminoplasty procedures to treat patients suffering from a spinal disorder to provide stabilization and decompression. The components of the surgical system may be monolithically formed, integrally connected or include fastening elements and/or instruments, for example, as described herein.

Implant 10 includes a first member, such as, for example, a first plate 12. Plate 12 extends between a first end 14 and a second end 16. End 14 includes a flange 18. Flange 18 includes an aperture 19. Flange 18 is configured for attachment to vertebral tissue, such as, for example, a lateral mass of a vertebral level via a bone fastener, such as, for example, a bone screw 20 (FIG. 6) configured for disposal in aperture 19.

End 16 includes a flange 22. Flange 22 includes an inner surface 24 that defines an oblong opening 26. It is contemplated that inner surface 24 can be smooth, even, arcuate, undulating and/or textured according to the requirements of a particular application. Plate 12 includes an arcuate intermediate portion 28 having a surface 30 that defines a recess 32. Portion 28 is configured for disposal about vertebrae. Recess 32 is configured to provide clearance for a tool, such as, for example, a burr used to cut bone disposed adjacent plate 12. Plate 12 has a rectangular cross section. It is contemplated that plate 12 can have alternate configurations, such as, tubular, oval, oblong, triangular, square, polygonal, irregular, uniform, non-uniform, variable, hollow and/or tapered.

A second member, such as, for example, a second plate 34 extends between a first end 36 and a second end 38. Plate 34 extends in substantial axial alignment with plate 12 such that plates 12, 34 overlap. It is contemplated that plate 34 can have alternate orientations, relative to plate 12, such as, for example, perpendicular, converging, diverging and/or other angular orientations such as acute or obtuse, co-axial and/or may be offset or staggered and may extend in alternate configurations such as, for example, having a radius of curvature, offset and/or staggered.

End 36 includes a flange 40. Flange 40 includes an aperture 41. Flange 40 is configured for attachment to vertebral tissue, such as, for example, a lateral mass of a vertebral level via a second bone fastener, such as, for example, a bone screw 42 (FIG. 6) through aperture 41. A second flange 44 is disposed at end 38. Flange 44 includes an inner surface 46 defining an oblong opening 48. It is contemplated that inner surface 46 can be smooth, even, arcuate, undulating and/or textured according to the requirements of a particular application. Plate 34 includes an arcuate intermediate portion 50. Portion 50 includes a surface 52 that defines a recess 54. Portion 50 is configured for disposal about vertebrae. Recess 54 is configured to provide clearance for a tool for cutting bone disposed adjacent plate 34. Plate 34 has a rectangular cross section. It is contemplated that plate 34 can have alternate configurations, such as, tubular, oval, oblong, triangular, square, polygonal, irregular, uniform, non-uniform, variable, hollow and/or tapered.

Flange 22 includes a first locking part, such as, for example, a knurled surface 56 that has a frictional surface configuration. It is envisioned that flange 22 may include alternative surface configurations, such as, for example, rough, arcuate, undulating, mesh, porous, semi-porous, dimpled and/or textured according to the requirements of a particular application.

Flange 44 includes a second locking part, such as, for example, a knurled surface 58 that has a frictional surface configuration. It is envisioned that flange 44 may include alternative, such as, for example, rough, arcuate, undulating, mesh, porous, semi-porous, dimpled and/or textured according to the requirements of a particular application. Surface 56 engages surface 58 such that flange 22 is movable relative to flange 44 such that plates 12, 34 are relatively translatable between a first configuration and a second configuration. In one embodiment, upon fixed engagement by, for example, fastener fixation, plates 12, 34 are disposed in a locked configuration to prevent contraction and/or expansion of plates 12, 34. It is contemplated that the prevention of contraction and/or expansion of plates 12, 34 includes resisting contraction and/or expansion of plates 12, 34.

In operation, flanges 22, 44 are configured for engagement such that openings 26, 48 are disposed in substantial alignment. Surfaces 56, 58 are disposed in alignment such that surfaces 56, 58 engage for a provisional fixation, which allows relative slidable movement therebetween upon force application to plates 12, 34. It is contemplated that the force application may be oriented laterally, axially, angular and/or in a plurality of body planes, such as, for example, sagittal, coronal and transverse.

A third bone fastener, such as, for example, a bone screw 60 is disposable with openings 26, 48 and configured to penetrate tissue, such as the spinous process of vertebrae. Disposal of screw 60 with openings 26, 48 provisionally fixes plates 12, 34 in assembly with vertebrae. Flange 22 of plate 12 is translatable relative to flange 44 of plate 34 between a first configuration (FIG. 5) and a second, expanded configuration (FIG. 7).

Figure 5:
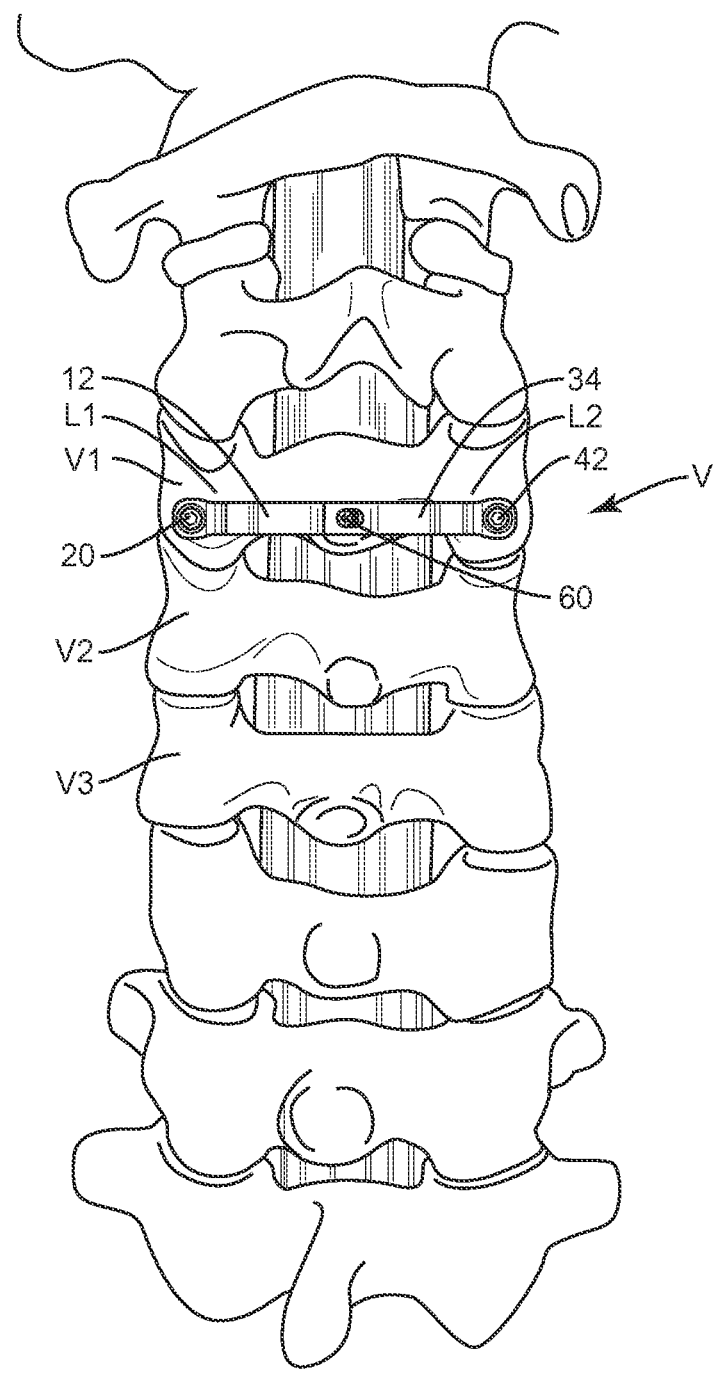
FIG. 5 is a plan view in part cross section of components of one embodiment of a system disposed with vertebrae in accordance with the principles of the present disclosure.
Figure 6:
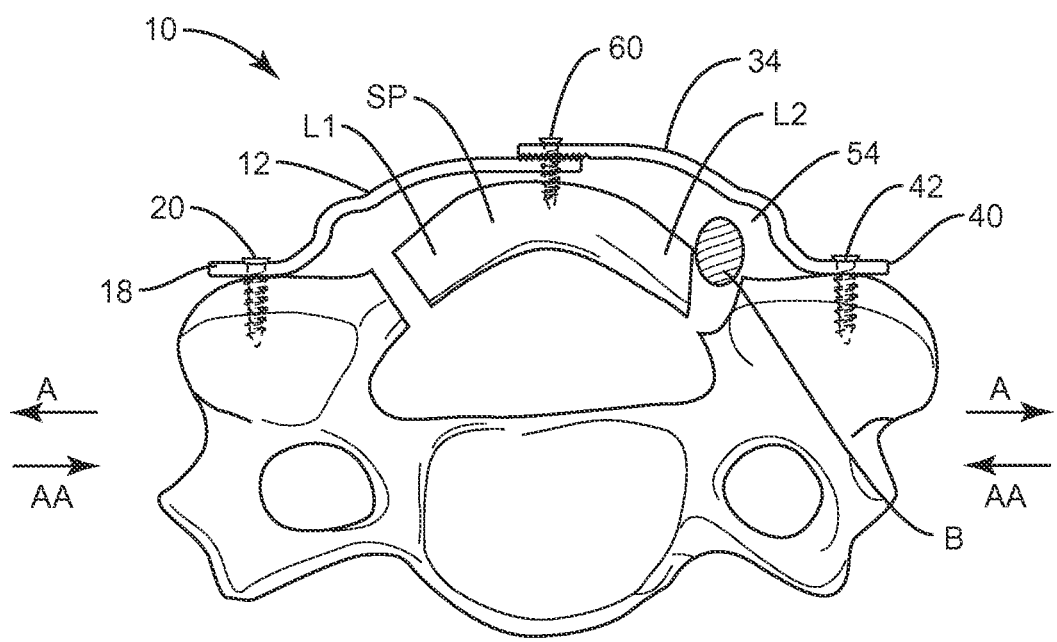
FIG. 6 is an axial view of the components and vertebrae shown in FIG. 5.

In a first configuration, as shown in FIG. 5, plates 12, 34 are disposed about a vertebral level and attached to tissue adjacent lamina. Upon desired positioning of each plate 12, 34, according to the requirements of a particular surgical application, screw 20 is disposed with tissue to attach flange 18 with tissue, for example, fastening screw 20 adjacent a lamina L1 of a vertebral level. Screw 42 is disposed with tissue to attach flange 40 with tissue, for example, fastening screw 42 adjacent a lamina L2 of the vertebral level. An instrument, such as, for example, a cutting burr B, as shown in FIG. 6, is utilized to cut selected portions of laminae L1, L2 laterally of a spinous process SP for a particular surgical treatment. Recesses 32, 54 facilitate access of cutting burr B to laminae L1, L2 upon provisional attachment of plates 12, 34 with vertebrae. The arcuate configuration of recess 32 allows cutting burr B to be positioned within recess 32 and between plate 12 and lamina L1 for cutting of lamina L1. The arcuate configuration of recess 54 allows cutting burr B to be positioned within recess 54 and between plate 34 and lamina L2 for cutting of lamina L2.

Cutting laminae L1, L2 relieves compression adjacent the vertebral level associated with laminae L1, L2. For example, expansion forces, in the direction shown by arrows A in FIG. 6, and/or contraction forces, in the direction shown by arrows AA, are applied to plates 12, 34 due to the decompression. Plates 12, 34 are caused to relatively translate such that surfaces 56, 58 slidably and frictionally engage such that plates 12, 34 expand to a second configuration, as shown in FIG. 7, or contract to a second configuration (not shown). Openings 26, 48 are substantially aligned and disposed over the spinous process SP. Screw 60 is further driven into spinous process SP to permanently fasten plates 12, 34 with the vertebral level.

Figure 7:
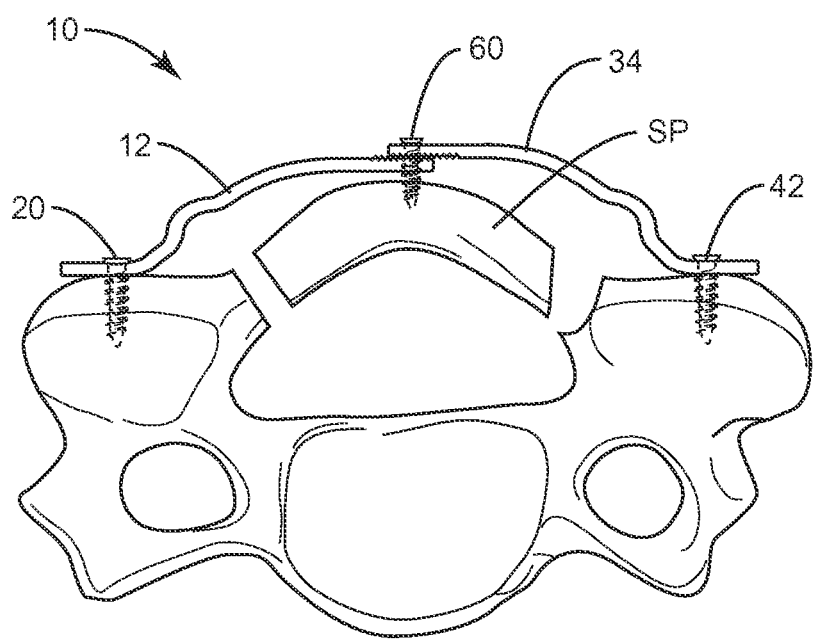
FIG. 7 is an axial view of the components and vertebrae shown in FIG. 6.

In use, as shown in FIGS. 5-7, the surgical system including implant 10, similar to that described above with regard to FIGS. 1-4, is employed with a surgical procedure, such as, for example, a laminoplasty treatment of a spine of a patient including vertebrae V. The surgical system may also be employed with other surgical procedures, such as, for example, discectomy, laminotomy, laminectomy, nerve root retraction, foramenotomy, facetectomy, decompression, and spinal, nucleus or disc replacement.

For example, implant 10 can be employed with a surgical procedure, such as, for example, a laminoplasty to alter one or more of the bony vertebral structures that surround and define the spinal canal. For example, vertebral levels V1, V2 and V3 of vertebrae V can be cut and/or weakened to open the canal and provide additional room for the spinal cord. In one embodiment, implant 10 stabilizes vertebral levels V1, V2 and V3 for proper healing.

In use, to treat the affected section of vertebrae V, a medical practitioner obtains access to a surgical site including vertebrae V in any appropriate manner, such as through incision and retraction of tissues. It is envisioned that the implant system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Implant 10 is then employed to augment the surgical treatment. Implant 10 can be delivered or implanted as a pre-assembled device or can be assembled in situ. Implant 10 can be completely or partially revised, removed or replaced in situ. It is contemplated that one or all of the components of the implant system can be delivered to the surgical site via manual manipulation and/or a free hand technique.

An incision is made in the body of a patient and a cutting instrument (not shown) creates a surgical pathway for delivery of implant 10 within the patient body to adjacent vertebral level V1.

In the first configuration, plates 12, 34 are positioned in alignment for attachment with vertebral level V1 for attachment to tissue adjacent lamina L1 and L2. A pilot hole or the like is drilled with lamina L1 and plate 12 is disposed such that aperture 19 is positioned in alignment with the pilot hole in lamina L1. Upon desired positioning of plate 12, according to the requirements of a particular surgical application, screw 20 is disposed with tissue to attach flange 18 with lamina L1.

A pilot hole or the like is drilled with lamina L2 and plate 34 is disposed such that aperture 41 is aligned with the pilot hole in lamina L2. Upon desired positioning of plate 34, according to the requirements of a particular surgical application, screw 42 is disposed with tissue to attach flange 40 with tissue.

Bone screw 60 is disposed with aligned openings 26, 48 and configured to penetrate spinous process SP of vertebral level V1. In one embodiment, spinous process SP can be shaved or otherwise treated to accommodate fastening of implant 10 with vertebral level V1. Disposal of screw 60 with openings 26, 48 provisionally fixes plates 12, 34 in assembly with vertebral V1. Flange 22 of plate 12 is translatable relative to flange 44 of plate 34 between a first configuration, as shown in FIG. 5 and a second, expanded configuration, as shown in FIG. 7.

In the first configuration, as shown in FIG. 5, plates 12, 34 are disposed about vertebral level V1 in an overlapping configuration and attached to tissue adjacent laminae L1, L2. A cutting burr B, as shown in FIG. 6, is utilized to cut selected portions of laminae L1, L2 laterally of spinous process SP for a particular surgical treatment. Recesses 32, 54 facilitate access of cutting burr B to laminae L1, L2 upon provisional attachment of plates 12, 34 with vertebral level V1, as described above.

Cutting laminae L1, L2 relieves compression adjacent laminae L1, L2. Expansion forces, in the direction shown by arrows A in FIG. 6, are applied to plates 12, 34 due to the decompression. Plates 12, 34 are caused to relatively translate such that surfaces 56, 58 slidably and frictionally engage such that plates 12, 34 expand to a second configuration, as shown in FIG. 7. Openings 26, 48 are substantially aligned and disposed over the spinous process SP. Screw 60 is further driven into spinous process SP to permanently fasten plates 12, 34 with vertebral level V1.

One or more of the components of the surgical system including implant 10 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of implant 10.

It is contemplated that the surgical system may include one or a plurality of bone fasteners for use with a single vertebral level or a plurality of vertebral levels. It is further contemplated that the bone fasteners may be engaged with vertebrae in various orientations, such as, for example, series, parallel, offset, staggered and/or alternate vertebral levels. It is envisioned that the bone fasteners may include one or a plurality of anchors, tissue penetrating screws, conventional screws, expanding screws, wedges, anchors, buttons, connectors, clips, snaps, friction fittings, compressive fittings, expanding rivets, staples, nails, adhesives, posts, fixation plates and/or posts.

In one embodiment, the surgical system includes an agent, which may be disposed, packed or layered within, on or about the components and/or surfaces of the surgical system including implant 10. It is envisioned that the agent may include bone growth promoting material, such as, for example, bone graft to enhance fixation of the fixation elements with vertebrae. It is contemplated that the agent may include one or a plurality of therapeutic agents and/or pharmacological agents for release, including sustained release, to treat, for example, pain, inflammation and degeneration. Upon completion of the procedure, it is contemplated that the non-implant components, instruments and assemblies are removed and the incision is closed.

Figure 8:
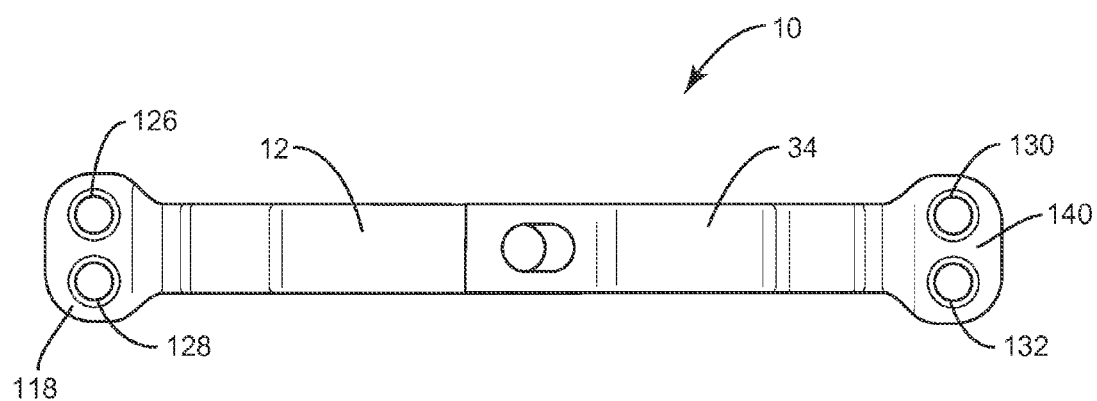
FIG. 8 is a plan view of components of one embodiment of a system in accordance with the principles of the present disclosure.

In one embodiment, as shown in FIG. 8, the surgical system includes implant 10, similar to the implant and methods of use described with regard to FIGS. 1-7, which includes flanges 118, 140. Flange 118 includes at least two apertures 126 and 128 for engagement with bone fasteners for attachment to tissue. Apertures 126, 128 are disposed in spaced apart relation equidistant from an edge surface of flange 118. Flange 140 includes at least two apertures 130 and 132 for engagement with bone fasteners for attachment to tissue. Apertures 130, 132 are disposed spaced apart relation equidistant from an edge surface of flange 140. It is envisioned that apertures 126, 128, 130, 132 may be variously disposed with flange 118 and not equidistant from the edge surface.

Figure 9:
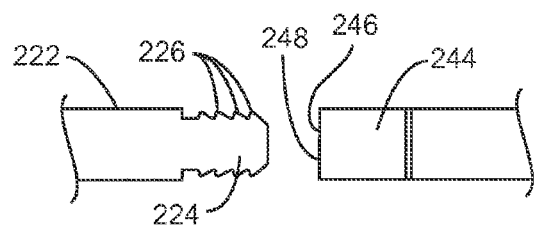
FIG. 9 is a break away, plan view of components of one embodiment of a system in accordance with the principles of the present disclosure.
Figure 10:
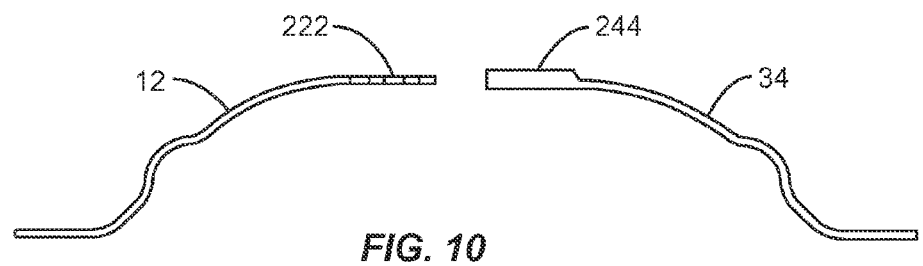
FIG. 10 is a side view of components shown in FIG. 9.

In one embodiment, as shown in FIGS. 9 and 10, the surgical system includes implant 10, similar to the implant and methods of use described with regard to FIGS. 1-7, which includes second flanges 222, 244 that include a ratchet configuration for engagement. As shown in FIG. 9, flange 222 includes a male ratchet portion 224 having teeth 226. Flange 244 includes a female ratchet portion having an inner surface 246 defining an opening 248. Surface 246 includes teeth (not shown) configured to engage teeth 226. As shown in FIG. 10, the ratchet configuration allows for selective incremental expansion and compression of plates 12 and 34.

Figure 11:
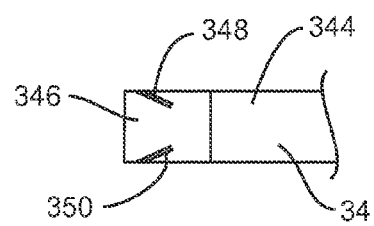
FIG. 11 is a break away, plan view of a component of one embodiment of a system in accordance with the principles of the present disclosure.
Figure 12:
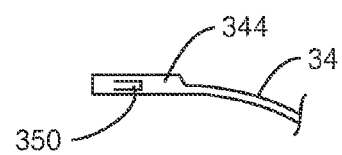
FIG. 12 is a side view of the component shown in FIG. 11.

In one embodiment, as shown in FIGS. 11 and 12, the surgical system includes implant 10, similar to the implant and methods of use described above, which includes a second flange 344 configured to engage in a ratchet configuration with flange 222, as discussed with respect to FIGS. 9 and 10. As shown in FIG. 11, flange 344 is configured to receive teeth 226. Flange 344 includes an inner surface 346 having angled tabs 348, 350. Tabs 348 and 350 are configured to engage teeth 226 for uni-directional selective incremental movement of plates 12 and 34, and fixation to prevent movement in an opposing direction.

Figure 13:
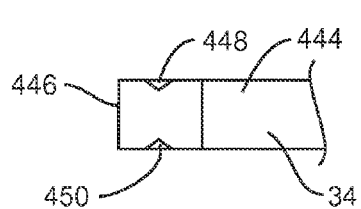
FIG. 13 is a break away, plan view of a component of one embodiment of a system in accordance with the principles of the present disclosure.
Figure 14:
FIG. 14 is a side view of the component shown in FIG. 13.

In one embodiment, as shown in FIGS. 13 and 14, the surgical system includes implant 10, similar to the implant and methods of use described above, which includes a second flange 444 configured to engage in a ratchet configuration with flange 222, as discussed with respect to FIGS. 9 and 10. As shown in FIG. 13, flange 444 is configured to receive ratchet portion 222. Flange 444 includes an inner surface 446 having dimpled protrusions 448 and 450. Protrusions 448 and 450 are configured to engage ratchet portion 222 for bi-directional selective incremental movement of plates 12 and 34 and fixation to prevent movement in an opposing direction.

Figure 15:
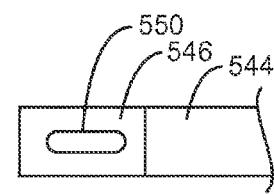
FIG. 15 is a break away, plan view of a component of one embodiment of a system in accordance with the principles of the present disclosure.
Figure 16:
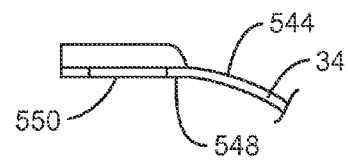
FIG. 16 is a side view of the component shown in FIG. 15.

In one embodiment, as shown in FIGS. 15 and 16, the surgical system includes implant 10, similar to the implant and methods of use described above, which includes a second flange 544 configured to engage in a ratchet configuration with flange 222, as discussed with respect to FIGS. 9 and 10. As shown in FIG. 15, flange 544 is configured to receive and engage teeth 226. Flange 544 includes an outer surface 546 having a top portion 546 and a bottom portion 548. An opening 550 is disposed in the top and bottom portions 546, 548. Opening 550 is configured to receive a bone screw for attachment to a spinous process.

Figure 17:
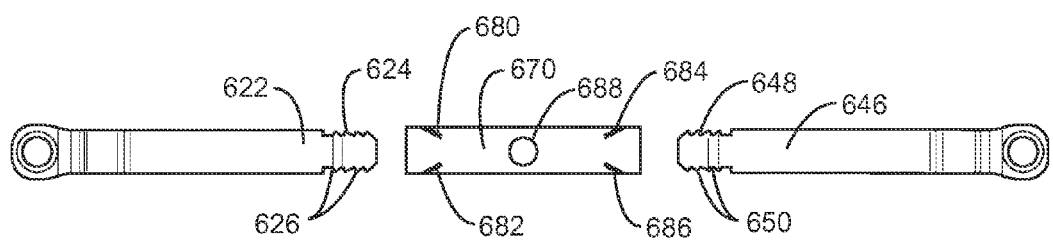
FIG. 17 is a plan view of components of one embodiment of a system, with parts separated, in accordance with the principles of the present disclosure.
Figure 18:
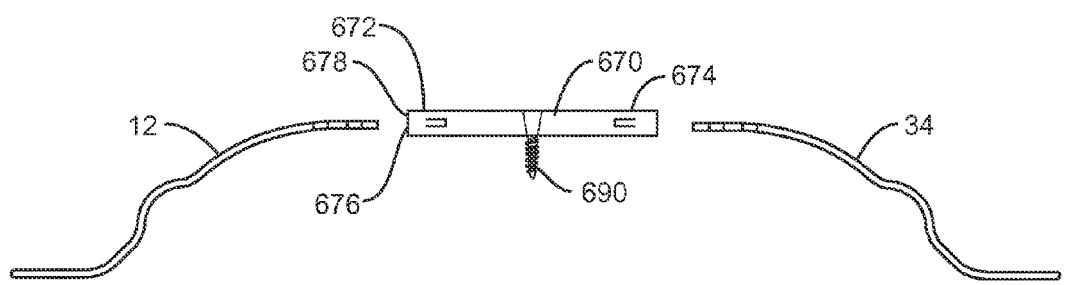
FIG. 18 is a side view of the components shown in FIG. 17.

In one embodiment, as shown in FIGS. 17 and 18, the surgical system includes implant 10, similar to the implant and methods of use described above, which includes second flanges 622 and 644 configured to engage in a ratchet configuration with a third member, such as, for example, a locking element 670. Flange 622 includes a ratchet portion 624 having teeth 626. Flange 644 includes a ratchet portion 648 including teeth 650. Locking element 670 includes a first end 672 and a second end 674. Locking element 670 includes an inner surface 676 that defines an opening 678. First end 672 includes tabs or protrusions 680 and 682. Tabs 680 and 682 are configured to engage teeth 626 for uni-directional and/or bi-directional incremental movement of plate 12 and fixation to prevent movement in an opposing direction. Second end 674 includes tabs or protrusions 684 and 686. Tabs 684 and 686 are configured to engage teeth 650 for uni-directional or bi-direction incremental movement of plate 34 and fixation to prevent movement in an opposing direction. An opening 688 is disposed through locking piece 670 and is configured to receive a bone screw 690 for attachment to a spinous process.

Figure 19:
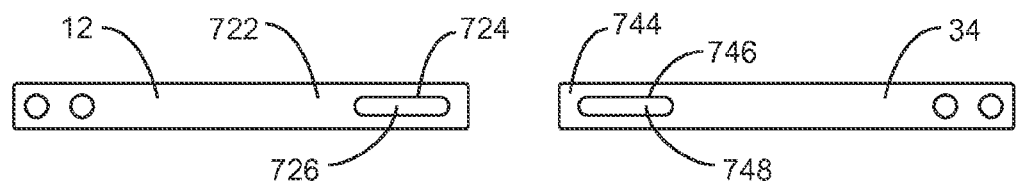
FIG. 19 is a plan view of components of one embodiment of a system, with parts separated, in accordance with the principles of the present disclosure.

In one embodiment, as shown in FIG. 19, the surgical system includes implant 10, similar to the implant and methods of use described above, which includes second flanges 722 and 744 configured to engage each other. Flange 722 includes a wall surface 724. Surface 724 defines an oblong opening 726. Flange 744 includes a wall surface 746. Surface 746 defines an oblong opening 748. An attachment mechanism, such as, for example a nut (not shown) is utilized to attached flange 722 with flange 744. It is contemplated that openings 726, 748 are configured for selective positioning of plates 12 and 34.

Figure 20:
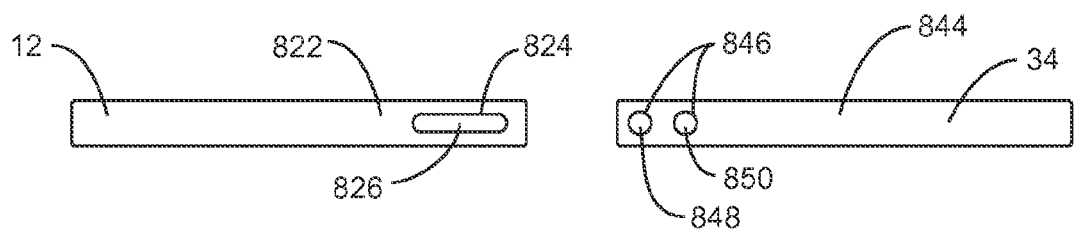
FIG. 20 is a plan view of components of one embodiment of a system, with parts separated, in accordance with the principles of the present disclosure.

In one embodiment, as shown in FIG. 20, the surgical system includes implant 10, similar to the implant and methods of use described above, which includes second flanges 822 and 844 configured to engage each other. Flange 822 includes a wall surface 824. Surface 824 defines an oblong opening 826. Flange 844 includes a wall surface 846. Surface 846 defines at least one opening 848, 850. Openings 848, 850 include a threaded inner surface for engagement with a screw (not shown). The screw engages flange 844 and flange 822. It is contemplated that opening 826 is configured for selective positioning of plates 12 and 34.

Figure 21:
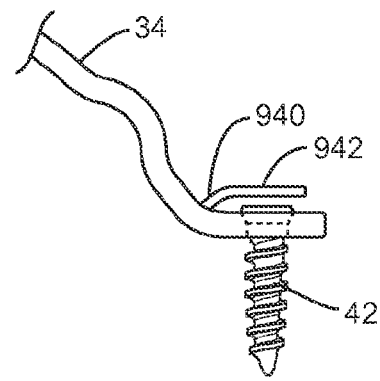
FIG. 21 is a side, break away view of a component of one embodiment of a system in accordance with the principles of the present disclosure.
Figure 22:
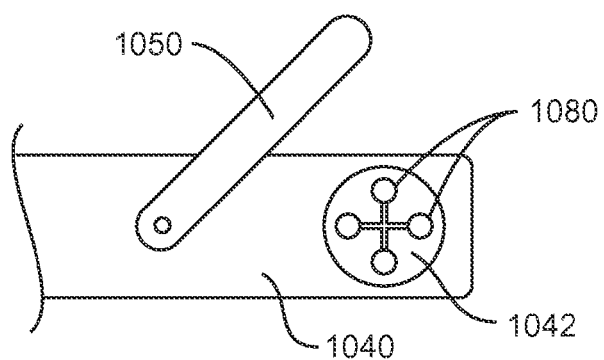
FIG. 22 is a break away, plan view of components of one embodiment of a system in accordance with the principles of the present disclosure.
Figure 23:
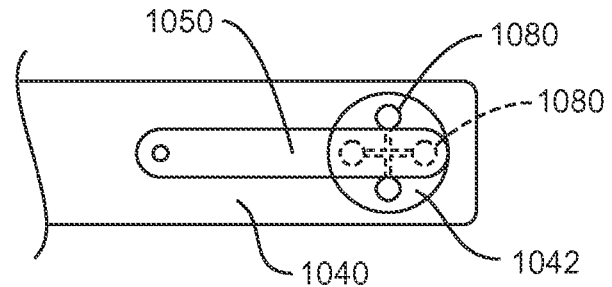
FIG. 23 is a break away, plan view of the component shown in FIG. 22.
Figure 24:
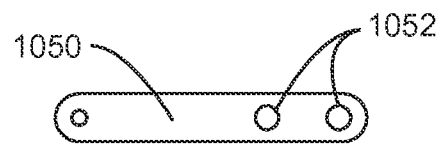
FIG. 24 is a plan view of components of one embodiment of a system in accordance with the principles of the present disclosure.
Figure 25:
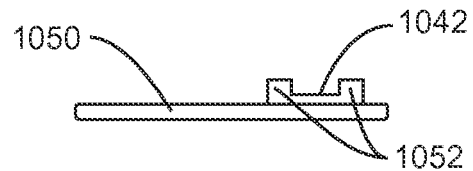
FIG. 25 is a side view of the component shown in FIG. 24.

In one embodiment, as shown in FIGS. 21-28, the surgical system includes implant 10, similar to the implant and methods of use described above, which includes an anti-backout mechanism for bone screws 20 and 42. In one embodiment, as shown in FIG. 21, plate 34 includes flange 940 having a swing tab or clip-on cover 942. Tab 942 prevents bone screw 42, fastened with tissue, from backing out of the tissue. In one embodiment, plate 12 includes an anti-backout configuration, similar to flange 940.

In one embodiment, as shown in FIGS. 22-25, the anti-backout mechanism includes plate 34 having a flange 1040 having a moveable bar 1050. Bar 1050 is configured to engage notches or slots 1080 disposed on screw 1042. Pin 1050 is configured to prevent bone screw 1042, fastened with tissue, from backing out of the tissue. In one embodiment, plate 12 includes an anti-backout configuration, similar to flange 1040. In one embodiment, bar 1050 includes pins 1052 configured to engage notches 1080 on screw 1042.

Figure 26:
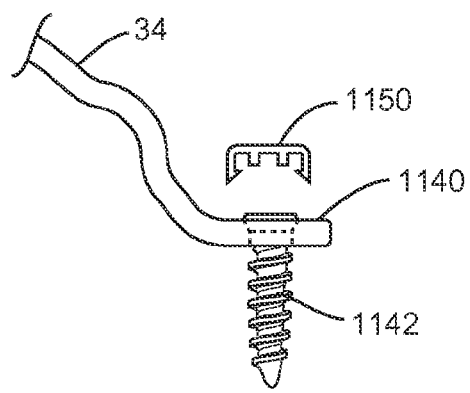
FIG. 26 is a break away, side view of components of one embodiment of a system in accordance with the principles of the present disclosure.
Figure 27:
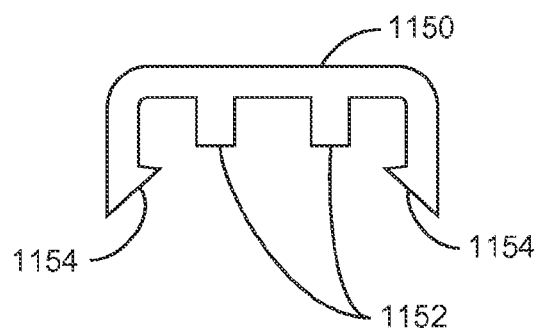
FIG. 27 is a side view of a component of the system shown in FIG. 26.
Figure 28:
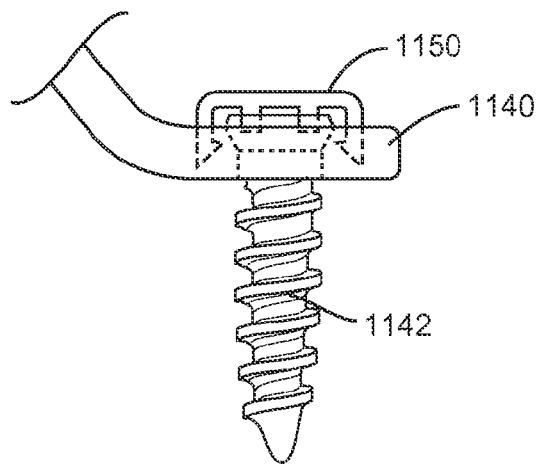
FIG. 28 is a break away, side view of components of the system shown in FIG. 26.

In one embodiment, as shown in FIGS. 26-28, the anti-backout mechanism includes plate 34 having flange 1140. Flange 1140 includes a cover plate 1150. Cover plate 1150 is configured to engage screw 1142. Cover plate 1150 includes pins 1152 configured to engage screw 1142. Cover plate 1150 includes barbs 1154 configured to engage flange 1140 to lock cover plate 1150 in place. In one embodiment, plate 12 includes an anti-backout configuration, similar to flange 1040.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A spinal implant comprising:
a first member extending between a first end configured for fixation with vertebral tissue adjacent a lamina and a second end, the first member comprising a substantially arcuate intermediate portion between the first and second ends, the intermediate portion including a surface that defines a recess configured to facilitate disposal of an instrument for engaging the lamina;
a second member extending between a first end configured for fixation with vertebral tissue adjacent the lamina and being disposed in spaced apart relation to the first end of the first member, and a second end being connected to the second end of the first member; and
a bone fastener,
wherein each of the second ends define a slot configured to be disposed in alignment with a spinous process, the bone fastener extending through the slots such that the bone fastener is adapted to penetrate the spinous process to fix the spinal implant to the spinous process prior to cutting a selected portion of the lamina and keep the spinous process in the same position after cutting,
wherein the second ends are relatively movable in a configuration such that the members are expandable and/or contractible the second ends each including knurled surfaces that are engageable to facilitate the relative movement.

2. A spinal implant as recited in claim 1, wherein the first end of the first member and the first end of the second member each comprise a flange, the flanges extending parallel to one another.

3. A spinal implant as recited in claim 2, wherein the flanges each include an aperture extending therethrough configured for disposal of a bone screw.

4. A spinal implant as recited in claim 3, wherein the apertures each include a countersink portion.

5. A spinal implant as recited in claim 1, wherein:
first end of the second member comprises a flange defining an opening;
the implant further comprises a bone screw configured for disposal in the opening and penetration in a lateral mass of the vertebral tissue; and
the flange includes a moveable bar configured to engage notches in the bone screw to prevent the bone screw from backing out of the vertebral tissue.

6. A spinal implant as recited in claim 5, wherein the moveable bar comprises pins that engage the notches in the bone screw to prevent the bone screw from backing out of the vertebral tissue.

7. A spinal implant as recited in claim 1, wherein the members include plates disposed in axial alignment.

8. A spinal implant as recited in claim 1, wherein the knurled surfaces define frictional surfaces that are engageable to facilitate the relative movement.

9. A spinal implant as recited in claim 1, wherein the knurled surfaces of the first member define a first locking part and the knurled surfaces of the second member define a second locking part, the parts being engageable to resist expansion and/or contraction of the members from an expanded configuration.

10. A spinal implant as recited in claim 1, wherein the first end of the first member includes a flange defining an opening configured for disposal of a fastener that fixes the first end with a lateral mass of the vertebral tissue.

11. A spinal implant as recited in claim 1, further comprising bone fasteners disposed with the first ends and configured to penetrate a respective lateral mass of the vertebral tissue, at least one of the first ends including a backout member configured for engagement with a respective bone fastener.

12. A spinal implant as recited in claim 1, wherein:
the first end of the second member comprises a flange defining an opening;
the implant further comprises a bone screw configured for disposal in the opening and penetration in a lateral mass of the vertebral tissue; and
the flange includes a swing tab configured to prevent the bone screw from backing out of the vertebral tissue.

13. A spinal implant as recited in claim 1, wherein:
first end of the second member comprises a flange defining an opening;
the implant further comprises a bone screw configured for disposal in the opening and penetration in a lateral mass of the vertebral tissue; and
the flange includes a clip-on cover configured to prevent the bone screw from backing out of the vertebral tissue.

14. A spinal implant as recited in claim 1, wherein the first end of the first member and the first end of the second member each comprise a flange comprising a pair of spaced apart openings positioned equidistant from an edge surface of the flange.

15. A spinal implant comprising:
a first plate including a first flange configured for fixation with a lateral mass adjacent a lamina of a vertebral level, a substantially arcuate intermediate portion and a second flange defining an opening, the intermediate portion including a surface that defines a recess configured to facilitate disposal of an instrument for engaging the lamina; and
a second plate including a first flange configured for fixation with a lateral mass of the vertebral level, an intermediate portion and a second flange defining an opening, the second flanges being engaged; and
a bone fastener extending through the openings and configured to penetrate a spinous process to fix the spinal implant to the spinous process prior to cutting a selected portion of the lamina and keep the spinous process in the same position after cutting,
wherein the second flange of the first plate is movable relative to the second flange of the second plate between a first configuration and a second configuration, the second flanges each including knurled surfaces that are engageable to facilitate the relative movement.

16. A spinal implant system comprising:
a first bone fastener;
a first plate including a first flange configured to be attached to a lateral mass adjacent to a lamina of a vertebral level via the first bone fastener, an arcuate intermediate portion defining a recess and a second flange defining an opening, the intermediate portion including a surface that defines a recess configured to facilitate disposal of an instrument for engaging the lamina;
a second bone fastener;
a second plate disposed in substantially axial alignment with the first plate, the second plate including a first flange configured to be attached to a lateral mass of the vertebral level via the second bone fastener, an arcuate intermediate portion defining a recess and a second flange defining an opening; and
a third bone fastener,
wherein the second flanges are engaged such that the third bone fastener is disposed with the openings and configured for penetrating a spinous process to fix the spinal implant to the spinous process prior to cutting a selected portion of the lamina and keep the spinous process in the same position after cutting,
wherein the second flange of the first plate is movable relative to the second flange of the second plate between a first configuration and a second, expanded configuration, the second flanges each including knurled surfaces that are engageable to facilitate the relative movement.

* * * * *